(12) United States Patent
Norrby et al.

(10) Patent No.: US 7,811,267 B2
(45) Date of Patent: Oct. 12, 2010

(54) KIT AND METHOD IN EYE SURGERY

(75) Inventors: Sverker Norrby, Leek (NL); Rolf Bergman, Uppsala (SE); Jöns Hillborn, Sigtuna (SE)

(73) Assignee: AMO Groningen B.V., Santa Ana, CA (US)

( * ) Notice: Subject to any disclaimer, the term of this patent is extended or adjusted under 35 U.S.C. 154(b) by 1960 days.

(21) Appl. No.: 10/438,618

(22) Filed: May 15, 2003

(65) Prior Publication Data

US 2004/0039399 A1 Feb. 26, 2004

Related U.S. Application Data

(60) Provisional application No. 60/381,297, filed on May 17, 2002.

(30) Foreign Application Priority Data

May 16, 2002 (SE) .................................. 0201479

(51) Int. Cl.
*A61M 35/00* (2006.01)
(52) U.S. Cl. .................. 604/289; 604/294; 602/74; 623/5.11; 623/5.13
(58) Field of Classification Search .............. 604/289, 604/294, 303–308; 602/48–50, 57, 74; 623/5.11–5.16
See application file for complete search history.

(56) References Cited

U.S. PATENT DOCUMENTS

| | | | | |
|---|---|---|---|---|
| 5,002,571 | A * | 3/1991 | O'Donnell et al. | 623/6.11 |
| 5,989,269 | A * | 11/1999 | Vibe-Hansen et al. | 606/151 |
| 6,387,379 | B1 * | 5/2002 | Goldberg et al. | 424/400 |
| 6,569,172 | B2 * | 5/2003 | Asculai et al. | 606/151 |
| 6,833,408 | B2 * | 12/2004 | Sehl et al. | 525/54.1 |
| 6,893,431 | B2 * | 5/2005 | Naimark et al. | 604/891.1 |
| 2002/0022883 | A1 * | 2/2002 | Burg | 623/8 |

(Continued)

FOREIGN PATENT DOCUMENTS

WO        WO 9222312        12/1992

(Continued)

OTHER PUBLICATIONS

Gwon et al, *Journal of Cataract and Refractive Surgery*, 19(11):735-746 (1993).

*Primary Examiner*—Justine R Yu
*Assistant Examiner*—Lynne Anderson

(57) ABSTRACT

A kit is provided, which comprises a) a collagen patch and b) an adhesive composition comprising (i) fibrin, fibrinogen or a combination thereof, and (ii) a biocompatible polymer capable of forming a viscous aqueous solution.

Also provided is use of the kit for the preparation of a sealing device for use in ophthalmic surgery to replace a natural lens which has been removed, in which sealing device the collagen patch of the kit is adapted to seal an opening in a capsular bag of an eye while admitting the entrance of an injection device through the opening for injection of a lens-forming material into the capsule; and in which sealing device the adhesive composition of the kit is adapted to be applied to the collagen patch so as to enable adhesion of the collagen patch to the capsular bag.

Also provided are methods for sealing an opening in a capsular bag of an eye, in which methods the kit is employed.

28 Claims, 4 Drawing Sheets

U.S. PATENT DOCUMENTS

2002/0153632 A1 * 10/2002 Schaufler .................... 264/50

FOREIGN PATENT DOCUMENTS

| WO | WO 9947185 | 9/1999 |
| WO | WO 0022459 | 4/2000 |
| WO | WO 0022460 | 4/2000 |
| WO | WO 0049976 | 8/2000 |
| WO | WO 0243630 | 6/2002 |

* cited by examiner

KIT AND METHOD IN EYE SURGERY

RELATED APPLICATION

The present application claims priority under 35 U.S.C. §119 of U.S. Application Ser. No. 60/381,297 filed May 17, 2002.

FIELD OF THE INVENTION

The present invention relates to the provision of a sealing device adapted to seal an opening in a capsular bag, which sealing device may advantageously be used in surgical processes that involve insertion of a lens-forming composition for replacement of a natural lens and for forming an intraocular lens implant.

BACKGROUND

Methods for removing a cataracteous and/or presbyopic natural lens from the capsular bag of the eye and replacing it by a lens-forming liquid material injected directly into the capsular bag are under development. Such methods have been described for example in Swedish patent application SE 0001934-9. The liquid material is a partially polymerized material, which can undergo a curing process in the eye and thereby form a solid lens implant. The lens implant acts as a substitute for the natural lens and aims to substantially restore the features of the natural lens of a young eye. Materials and methods suitable for injection and subsequent formation of an IOL (intraocular lens) are disclosed in WO00/22460, WO00/22459, WO99/47185 and in SE 0001934-9. A defect natural lens matrix can be removed by conventional surgical methods, e g involving an ultrasound probe, such as a phacoemulsification method involving aspiration. In order to facilitate the removal of the lens matrix and the refilling with lens-forming liquid material, a capsulotomy, typically a capsulorhexis, is prepared in the anterior wall of the capsular bag. The capsulorhexis is prepared from a circular or essentially circular capsulotomy in the capsular bag wall, typically with a diameter of from about 0.5 to about 2.5 mm. Subsequently, an injection syringe needle is inserted through an incision in the eye and through the capsulorhexis into the capsular bag, and the lens-forming liquid material injected into the capsular bag.

It has been identified as a problem in capsular bag filling processes that liquid material can leak through the capsulorhexis during the injection and before the final lens is formed. For this purpose, a plug is proposed in the Japanese patent specification JP97-308946. This plug is adapted to be attached to the injection syringe needle and inserted into the eye, and positioned in the right position in the rhexis when the syringe needle is inserted. Since the plug is relatively large and adapted to stay in the rhexis permanently, optical problems could arise. Furthermore, it needs a relatively large opening in the eye to be implanted. The plug also comprises a filling tube, which has to be cut off after filling. The tube could cause a leak. The size of the plug may also influence the free movement of the capsule that is needed for even deformation of the capsule during accommodation.

In WO00/49976, a more simple plug construction is suggested, which attempts to act as a valve during the surgical process. This plug, too, suffers from the drawback that parts of its structure are permanently located outside the capsular bag after finalization of the surgery. The curved flexible member is permanently protruding from the capsular bag through its hub-like attachment point to the flexible discoid flap-valve member. Consequently, the protruding parts may risk to compromise surrounding delicate eye tissues, including the iris, while they also risk generating unwanted optical side effects.

In a study of lens regeneration in rabbits and cats, A Gwon and co-workers used a collagen patch to seal a capsulotomy (J Cataract Refract Surg 19:735-745). Lens extraction was performed through an anterior capsulotomy, and the capsulotomy was sealed with a collagen patch. In some of the animals studied, the fibrin sealant Tissucol® (Immuno AG) was applied over the collagen patch subsequent to the application thereof. The injection of a lens-forming composition into the capsule in connection with the capsulotomy is not discussed, since the object of the conducted experiments was the study of spontaneous lens regeneration. Thus, the circumstances of these experiments differ in many respects from those of a surgical procedure contemplated in the context of the present invention. The differences include, among other things, that in the experiments of Gwon et al, a gas was injected into the capsule. Furthermore, the capsulotomy prepared was of a size significantly larger than that used in lens replacement surgery. Also, keeping a collagen patch in place in experiments with empty lens capsules, such as those described by Gwon et al, differs substantially from the situation encountered when a plug is applied to stop leakage of an injected lens-forming composition, inter alia because of the pressure exerted by such material on the capsulorhexis plug from inside the capsule.

Thus, there remain problems with known plug parts or sealing means for an opening in the capsular bag in the context of capsular filling processes. Accordingly, there is a need for improvements in such plug parts or sealing means.

SUMMARY OF THE INVENTION

It is an object of the present invention to meet this demand through providing improved tools for sealing an opening in a capsular bag of an eye in connection with injection of lens-forming composition into the eye capsule, and especially to provide a sealing device for opening in the capsular bag of the eye that effectively prevents a liquid inserted into the capsular bag to leak out through the opening.

It is also an object of the present invention to provide a sealing device for such an opening, which device leaves no parts permanently located outside of the capsular bag after the lens implantation process is finalized.

Another object is to provide a sealing device having means by which its location can be controlled after insertion thereof throughout the capsule filling process and lens-forming process.

Yet another object of the present invention is to provide a sealing device which consists mainly of biocompatible materials. Furthermore, it is an object that the sealing device should be biodegradable, such that it does not leave any traces some time after completion of the lens-forming process.

A further object of the invention is to provide methods employing such tools for the efficient sealing of an opening in the capsular bag of an eye.

For these and other objects that will be apparent from the following disclosure, the present invention in one aspect provides a kit comprising a) a collagen patch and b) an adhesive composition comprising (i) fibrin, fibrinogen or a combination thereof, and (ii) a biocompatible polymer capable of forming a viscous aqueous solution. In a related aspect of the invention, the kit of the invention is intended for use in ophthalmic surgery. Yet a related aspect of the invention provides use of the kit of the invention for the preparation of a sealing device for use in ophthalmic surgery to replace a natural lens which has been removed, in which sealing device the collagen patch of the kit is adapted to seal an opening in a capsular bag of an eye while admitting the entrance of an injection device through the opening for injection of a lens-forming material into the capsule; and in which sealing device the adhesive composition of the kit is adapted to be applied to the collagen patch so as to enable adhesion of the collagen patch to the capsular bag.

Further aspects of the invention relate to methods for sealing of an opening in a capsular bag of an eye in connection with ophthalmic surgery. Thus, one of these aspects provides such a method in connection with ophthalmic surgery to replace a natural lens with a lens-forming composition, through injection thereof into the lens capsule through the opening. The method comprises:

- introducing a collagen patch into the lens capsule through the opening, said collagen patch being adapted to seal the opening from the inside of the capsular bag;
- adjusting the location of the collagen patch with an adjusting means operable from the outside of the capsular bag, so that the collagen patch at least partly covers the opening in the capsular bag;
- displacing and/or deforming the collagen patch to admit passage into the capsular bag of the lens-forming composition;
- repositioning the collagen patch so that it seals the opening in such a way that displacement of a lens-forming composition to the outside of the capsule is prevented;
- applying an adhesive composition, comprising (i) fibrin, fibrinogen or a combination thereof and (ii) a biocompatible polymer capable of forming a viscous aqueous solution, to the collagen patch and/or the capsular bag to provide adhesion of the collagen patch to the capsular bag, thereby ensuring sealing of the opening.

In a related aspect of the invention, another method for sealing of an opening in a capsular bag of an eye in connection with ophthalmic surgery to replace a natural lens with a lens-forming composition, through injection thereof into the lens capsule through the opening, is provided. This method comprises:

- introducing a collagen patch into the lens capsule through the opening, said collagen patch being adapted to cover the opening from the inside of the capsular bag and to function as a septum for injection of a lens-forming composition therethrough;
- adjusting the location of the collagen patch with an adjusting means operable from the outside of the capsular bag, so that the collagen patch covers the opening in the capsular bag;
- applying an adhesive composition, comprising (i) fibrin, fibrinogen or a combination thereof and (ii) a biocompatible polymer capable of forming a viscous aqueous solution, to the collagen patch and/or the capsular bag to provide adhesion of the collagen patch to the capsular bag, thereby ensuring sealing of the opening.

In yet another related aspect of the invention, a method for sealing of an opening in a capsular bag of an eye in connection with ophthalmic surgery is provided. This method comprises:

- covering the opening with a collagen patch, the collagen patch being applied from the outside of the capsular bag;
- applying an adhesive composition, comprising (i) fibrin, fibrinogen or a combination thereof and (ii) a biocompatible polymer capable of forming a viscous aqueous solution, to the collagen patch and/or the capsular bag to provide adhesion of the collagen patch to the capsular bag, thereby ensuring sealing of the opening.

The various aspects of the present invention make possible the efficient sealing of a capsular bag. The provision of a novel kit comprising biocompatible components that are friendly to eye tissue is beneficial, in that such materials are likely to promote the healing process after eye surgery. Furthermore, a minimal disturbance of the optical properties of the eye may be obtained, since the combination of materials used is biodegradable and will not remain in the eye as a potential disturbance of said optical properties. However, during the healing process after eye surgery and before degrading of the materials of the kit according to the invention, the sealing device prepared therefrom is flexible enough that it will follow the accommodative movements of the lens capsule.

DETAILED DESCRIPTION OF EMBODIMENTS OF THE INVENTION

As described above in the summary, the present invention provides a kit comprising a collagen patch and an adhesive composition based on fibrin or fibrinogen, which adhesive composition also comprises a biocompatible polymer capable of conferring viscous properties to the adhesive composition.

The adhesive composition to be combined with a collagen patch in the preparation of a sealing device is preferably one similar to that which is described in WO92/22312, hereby incorporated by reference. Thus, the adhesive composition advantageously further comprises factor XIII, as well as a thrombin component. The biocompatible polymer is preferably provided in an amount such that an aqueous solution formed from said composition has a viscosity of from 500 to 1 000 000 centipois, said viscosity range being preferred for reasons of convenient application of the adhesive composition. Furthermore, such a viscosity is advantageous in the use of the kit in eye surgery or in the methods of the invention, since it ensures that the adhesive composition is not displaced from its area of application, i e does not flow. The biocompatible polymer is advantageously a polysaccharide or a proteoglycan, which furthermore preferably does not interfere with the process of fibrin clotting. Among such polysaccharides, special mention is made of xanthan, dextran, cellulose and glycosaminoglycans, as well as salts and derivatives thereof. An especially preferred polysaccharide is hyaluronic acid, or a salt or derivative thereof. Employing the well known and well characterized hyaluronic acid in the adhesive composition of the kit according to the invention has particular advantages in terms of biocompatibility and ease of healing after surgery.

The kit according to the invention further comprises a collagen patch. The collagen patch may be provided with removable adjusting means, which are connected to the patch and through manipulation of which it is possible to position the patch to a desired location. The removable adjusting means may for example consist of at least one flexible thread attached to the collagen patch, and optionally protruding from the collagen patch. In order to be suitable for use in the preparation of a sealing device for use in ophthalmic surgery, the collagen patch should be adapted to allow the passage through or beside the patch of an injection device, or of a lens-forming material. To this end, the collagen patch may be adapted to function as a septum, through which a syringe needle, or any other injection device sharp enough to penetrate the patch, may pass. Advantageously, this may entail no special treatment of the collagen, since its properties makes it inherently suitable to function as a septum. However, depending on the exact type of collagen used, such treatment may in some cases be necessary. As an alternative, the collagen patch may be provided with a cut, which is adapted to admit passage of an injection device therethrough. In some embodiments, this cut is provided with an overlapping part, adapted to seal the cut when injection of lens-forming material is completed, in order to prevent undesired leakage of injected lens-forming composition through the cut.

The collagen material of the kit according to the invention should furthermore preferably be sufficiently thin to follow the accommodation movements of the capsular bag when the kit is used in the preparation of a sealing device for eye surgery. Normally, that means that the collagen patch will have a thickness in the range of from about 5 to 0.250 micrometers. The collagen patch may have any shape suitable for covering of an opening in a capsular bag of an eye in connection with eye surgery. However, it is preferred that the collagen patch is provided essentially in the form of a disc. Such a collagen disc may for example have a diameter of 0.5-3 mm. In the case of a collagen patch that is used in the preparation of a sealing device for a capsular bag opening, it is foreseen that dimensions roughly corresponding to those given above will be suitable, also for collagen patches that are not disc-shaped. The skilled person is capable of ascertaining the appropriate size of the collagen patch with knowledge of the size of the opening that is to be sealed.

The above embodiments of the components of the kit according to the invention are to be seen as general, and not explicitly limited by any particular use of the kit. In the following, further possible designs and adaptations of the components are described, which are directly related to the use according to the invention of said kit in ophthalmic surgery, and also in the specific surgical methods of the invention.

As described in the summary, the invention, in one of its aspects, provides use of a kit according to the first aspect of the invention for the preparation of a sealing device for use in ophthalmic surgery to replace a natural lens which has been removed, in which sealing device the collagen patch of the kit is adapted to seal an opening in a capsular bag of an eye while admitting the entrance of an injection device through the opening for injection of a lens-forming material into the capsule; and in which sealing device the adhesive composition of the kit is adapted to be applied to the collagen so as to enable adhesion of the collagen to the capsular bag.

In connection with this use of the kit, the collagen patch is preferably adapted to cover the entire opening in the capsular bag, notwithstanding that in some cases it may also be beneficial to cover only a part of the opening. In order not to disturb the optical properties of the eye, the opening is preferably situated off the optical axis of the eye. Since openings in capsular bags in connection with the type of surgery contemplated are of the order of 1 mm in size, the collagen patch is preferably adapted to cover an opening of about 1 mm in diameter. The collagen patch may be adapted to be placed on the inside or outside of the opening, depending on the specific circumstances. It is likely that a given collagen patch comprised in a kit according to the invention may just as easily be applied inside the capsular bag as outside. The correct positioning of the patch is easily determined by the attendant surgeon, taking into consideration among other things the ease of application of adhesive composition in order to provide adhesion of the patch to the capsular bag.

In the use of the kit according to this aspect of the invention, the collagen patch of the kit is preferably provided with a removable adjusting means in the form of at least one flexible thread, said at least one thread being of such a length that it protrudes outside of the eye and can be manipulated from outside the eye when the collagen patch is positioned to seal the opening. Such manipulation is particularly desired in the case when the collagen patch is inserted into the capsular bag in order to seal the opening from the inside. As noted above, the adjusting means is typically one or several thin flexible wire(s), non-permanently attached to the collagen patch. In a suitable embodiment, the thin wire penetrates the patch from the anterior to the posterior side and then penetrates the patch from the posterior to the anterior side. The distance between the two penetrating positions and their locations on the patch are selected so that it can be comfortably manipulated, either with a micro-forceps or with other suitable means, also from outside of the eye. It is to be understood that the thin wire can be of such a length that it protrudes out of the eye through a corneoscleral incision. The wire is preferably made of a less flexible material than the collagen of the patch or the material of the capsular bag, and is attached to the patch in a manner that it is easily removable when the lens-forming material is introduced, or when then lens-forming process is finalized. Typically suitable materials for the wire are different brands of nylons that are well known in surgical processes and not discussed in further detail in the present text.

In keeping with an object of the invention, the sealing device prepared using the present kit is preferably biodegradable. This is made possible by the employment of the materials mentioned above in connection with the description of preferred embodiments of the kit. Preferably, the sealing device prepared is such that it is degraded within three weeks of being placed in or on a lens capsule. For example, it may be such that it is degraded within one week of being placed in or on a lens capsule. In a preferred embodiment of a sealing device prepared using the kit of the invention, the sealing device is degraded after completion of lens formation. The time needed for lens formation to be completed will depend on what lens-forming composition is used, but will normally not exceed the three weeks designated above as a preferred time frame for degradation of the sealing device.

In the use of the kit according to the invention for the preparation of a sealing device, the adhesive composition of the kit is adapted to be applied to the collagen patch. One of the purposes of the adhesive composition is to serve as a contacting means, to establish an improved contact between the surface of the collagen patch and the wall of the capsular bag, so as to prevent or hinder any displacement of the patch as a result of forces exerted on the capsular bag wall during the accommodation process. In order to ensure correct accommodation processes, the forces exerted on the capsular bag need to be transmitted correctly without any dead zones incapable of participating in the process. When a very soft lens material is employed, which has a sufficiently low elasticity modulus to form accommodating lens, this type of dead zones during accommodation may eventually result in that the lens material does not correctly participate in accommodation, or at worst will bulge out anteriorly with uncontrollable consequences. Thus, in order to alleviate any such detrimental effects, the collagen patch is provided with an adhesive composition to improve the contact between the patch and the wall of the capsular bag. A further function of the adhesive composition, in connection with use of the kit for preparation of a sealing device, is to eliminate undue stress to ocular tissues during the early post-operative period, through fixing the collagen patch during the time of lens-forming.

As further described in the summary, the invention provides three methods for sealing of an opening in a capsular bag, which methods employ the combination of a collagen patch and a fibrin- or fibrinogen-based adhesive composition.

The first of these methods is based on the presumption that the lens-forming material be injected beside, rather than through, the collagen patch, which necessitates the displacement and/or deformation of the patch to admit passage of the lens-forming composition. Furthermore, the collagen patch is introduced inside the capsular bag, for sealing of the opening from the inside. Suitably, the method comprises deforming the plug part so as to obtain a shape insertable through the opening. To properly adjust the position of the patch before, during and after injection of lens-forming composition, the patch is preferably provided with removable adjusting means as described above. Since the injection of lens-forming composition is dependent on the displacement and/or deformation of the patch, sealing of the opening through application of adhesive composition to the collagen patch and/or the capsular bag is not performed until such injection has been completed. In one embodiment, said deformation of the collagen patch is made easier by the provision of a cut in the patch, optionally with an overlapping part for easier sealing thereof. The cut preferably extends radially from the center of the patch to the circumference, in the case of a patch substantially having a disc shape.

In the second method according to the invention, the need for displacement and/or deformation of the patch is eliminated through adaptation of the patch to function as a septum. As described above, this may not entail any particular preparation of the collagen material, since it may well be adapted for such a function in its native state. In the method according to this aspect of the invention, the collagen patch is also inserted into the capsular bag to seal the opening from the inside. Suitably, the method comprises deforming the plug part so as to obtain a shape insertable through the opening. Also, it is preferable that the patch be provided with removable adjusting means as described above. However, in contrast to the case of the first method described, the adhesive composition is advantageously applied to the patch and/or capsular bag before injection of lens-forming composition through the patch, so that the patch is kept properly in place during injection, and in order to prevent any leakage of lens-forming composition.

The third method according to the invention is of a more generally applicable nature, concerning sealing of an opening in a capsular bag from the outside. The method comprises positioning a collagen patch so that it covers the opening in the capsular bag from the outside, whereupon an adhesive composition is applied to secure the position of the collagen patch and thereby ensure sealing of the opening. Of course, the method according to this aspect of the invention may well be used in connection with ophthalmic surgery to replace a natural lens with a lens-forming composition, through injection thereof into the lens capsule through the opening. Then, the opening may be sealed before injection, in which case the collagen patch is suitably adapted to function as a septum.

Any one of the methods according to the invention may also comprise a step in which an agent that counteracts secondary cataract formation is introduced in the capsular bag before sealing of the opening. Such agents are typically introduced with an injection syringe that can displace or deform the patch sufficiently to insert an injection needle in the capsular bag, or is sharp enough to penetrate the patch. The collagen patch provides a sufficiently sealed environment that the injected agent is prevented from coming in contact with other ocular tissues than the inner wall of the capsular bag during the secondary cataract treatment. Suitable agents are cytotoxic or antiproliferative agents that counteract growth of epithelial cells, which cells may compromise the transparency of the capsular bag after surgery. An example of such an agent is 5-fluorouracil, but numerous other agents are conceivable to the skilled person. Alternatively, an agent capable of blocking epithelial cell adhesiveness would be useful in this context, such as the calcium channel blocker mibefradil.

It is obvious that the present invention provides highly advantageous tools and methods for use in ophthalmic surgery, admitting a high degree of versatility and ready adaptation for numerous different surgical conditions, due to their simple construction and adaptability to the ocular environment. The following part aims to exemplify some specific embodiments of the kit according to one aspect of the invention which are intended to be illustrative, but not limiting for the scope of invention.

EXAMPLES OF EMBODIMENTS OF THE INVENTION

Figure 1A:
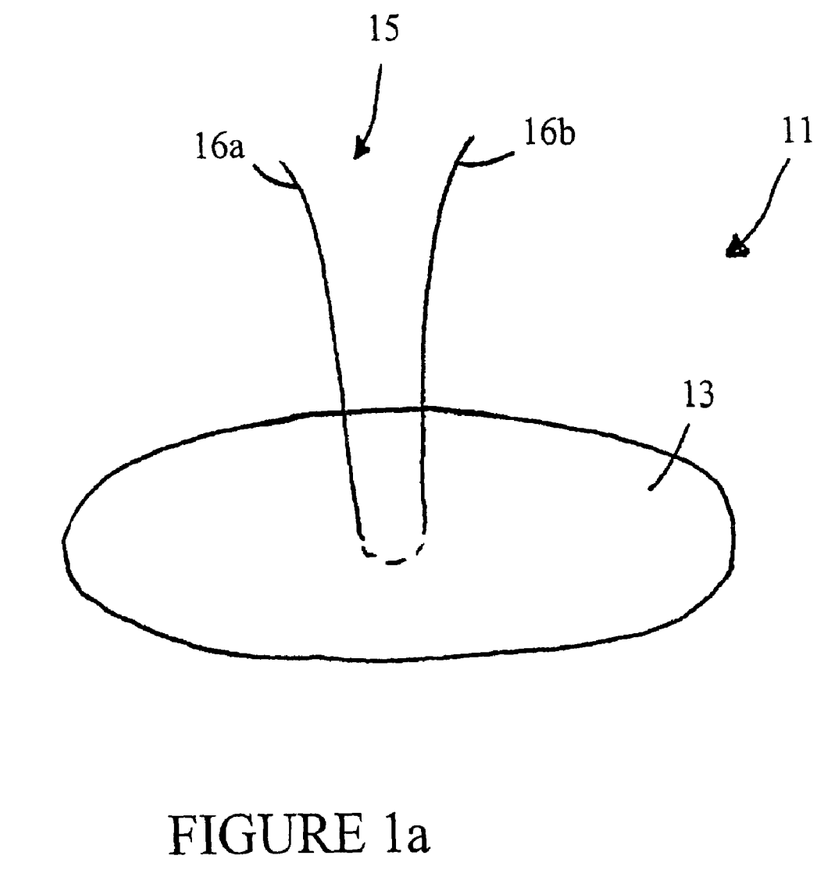
FIG. 1a is a schematic top view of a sealing device prepared using a kit according to an embodiment of the invention.

FIG. 1a is a schematic top view of a collagen patch forming part of a kit according to an embodiment of the invention, used to prepare a sealing device 11. The sealing device 11 comprises an essentially disc-shaped collagen patch 13 and an adjusting means 15. In this embodiment, the adjusting means 15 is a nylon thread attached at its middle to the center of the patch 13. For example, the thread may pass through two holes in the plug part 13, leaving the adjusting means 15 with two thread ends 16a and 16b pointing out from the patch 13 on the same side. The thread 15 could of course be attached to the plug part 13 in some other way, as well as being made from another material than nylon. It is also possible to attach one end only of the thread to the patch 13, leaving only one end pointing out from the patch 13. The nylon thread used in this embodiment has a stiffness suitable to enable manipulation of the collagen patch.

Figure 1B:
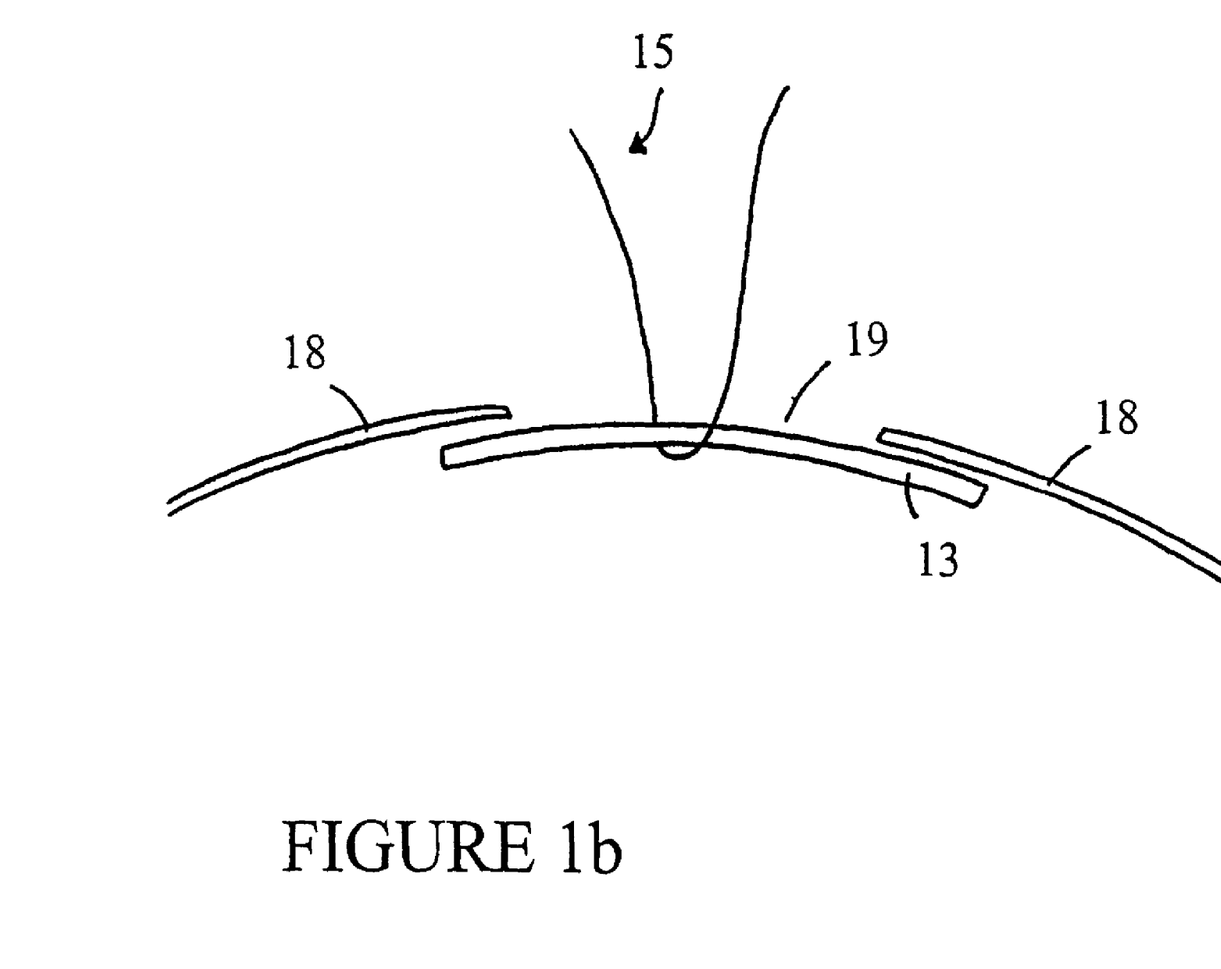
FIG. 1b is a side view of a sealing device comprising the collagen patch in FIG. 1a, which has been inserted into a capsular bag.

FIG. 1b is a side view of the sealing device 11 shown in FIG. 1a, inserted into a capsular bag 18. The patch 13 of the sealing device 11 is inserted inside the capsular bag and adapted to cover a opening 19 in the capsular bag from the inside. The nylon threads 16a, 16b extend in the anterior direction from the sealing device 11, and are preferably long enough to extend out of the eye. Thus, the sealing device 11 can be controlled and kept in the desired location from outside the eye. The sealing device 11 is adapted to be inserted into the eye before the lens-forming liquid material is injected and after the natural lens has been removed.

When the lens-forming material is injected in accordance with an embodiment of a method according to the invention, a delivering means, here an injection syringe, is used. The injection syringe needle is inserted through the eye and through the opening by displacing and/or deforming the sealing device enough that the needle may be admitted into the capsular bag. After injection, the syringe needle is removed out from the capsular bag and the eye. Subsequently, the adhesive composition of the kit used to prepare the sealing device is applied to the points of contact between the patch and the capsular bag. The seal thus prepared is aided by the pressure exerted by the fluid lens-forming material to maintain the original position and shape of the patch in front of the opening, thus preventing the lens-forming material to leak out. The lens-forming material may now be cured into the final lens implant, an the wire can be removed from the eye with e g forceps. To be noted is that the injection syringe does not actually need to be inserted all the way into the capsular bag. It is enough to inject the lens-forming material outside the opening in a direction towards the opening. Then the material will force itself through the opening beside the collagen patch and into the capsular bag. If a small amount of the material is nevertheless left in the anterior chamber of the eye, it will easily be flushed out by the rinsing liquid used in the surgical procedure.

The liquid lens-forming material may be a silicon material that will cure in ambient body temperature or through another curing mechanism, e g by means of photo-sensitizers activated by light of a selected wavelength as further described in WO00/22460. In this embodiment of a method according to the invention, wherein the collagen patch is adapted for sealing the opening from the inside of the capsular bag, the sealing device 11 is pressed against the inner wall around the opening of the capsular bag by the lens implant. After the surgical procedure is completed, the collagen patch is left in place, secured by the adhesive composition. The materials of the kit of the invention will subsequently be degraded, following a period of time needed for healing of the capsular bag wall opening.

Figure 2:
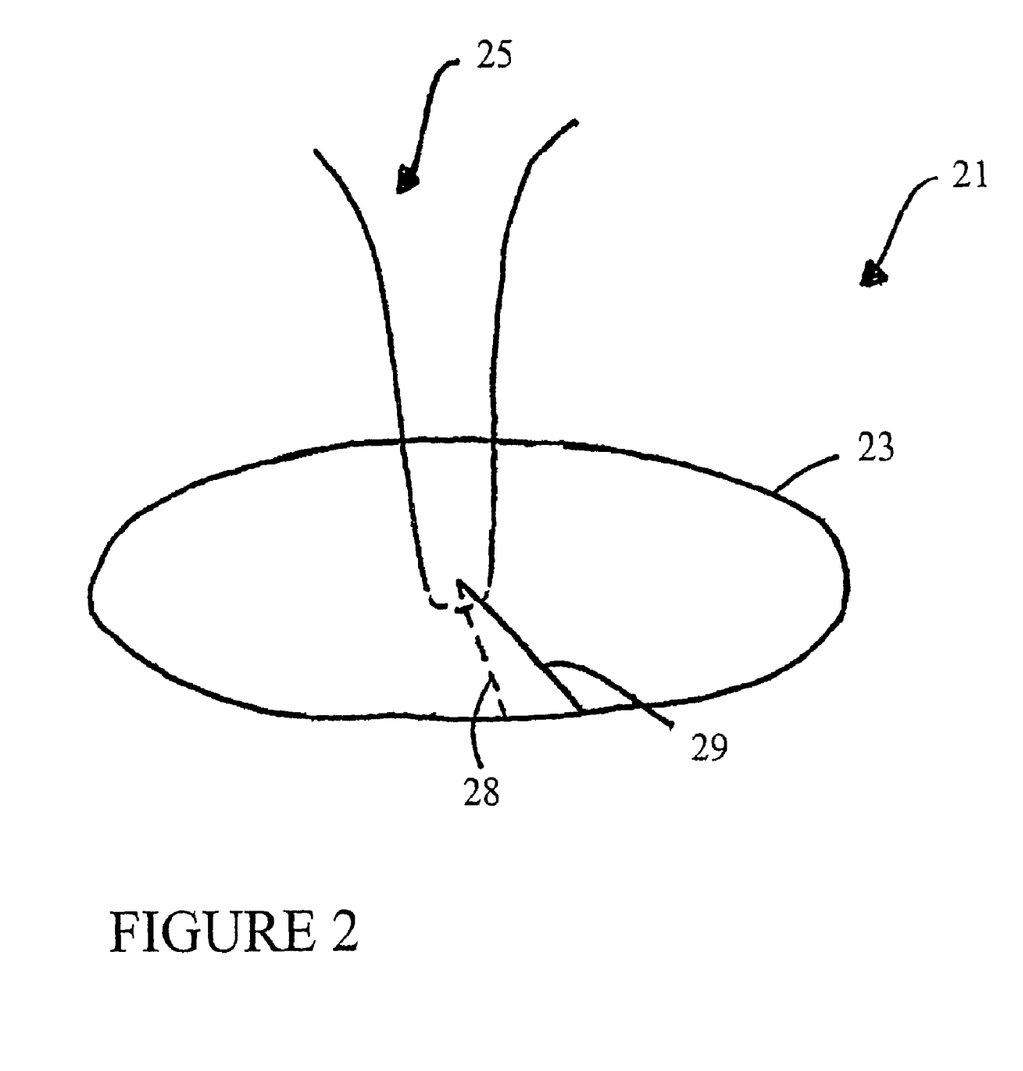
FIG. 2 is a top view of a sealing device prepared using a kit according to another embodiment of the invention.

FIG. 2 is a view from above of a sealing device 21 prepared using a kit according to another embodiment of the invention. This second embodiment principally follows the first embodiment of the sealing device, comprising a collagen patch 23 and an adjusting means 25. The materials and the dimensions are the same, as is the use of the sealing device. The difference is that the patch 23 further comprises a cut 29 along a radius of the disc-shaped patch 23. The purpose of the cut 29 is to facilitate entrance of the injection syringe needle through the opening during injection, and to minimize leakage of the injected material through the opening during injection. Preferably, the patch 23 is also provided with an overlapping part 28 under the cut 29. The purpose of the overlapping part 28 is to prevent material from leaking out through the cut 29 after removal of the needle. As explained above, it is not necessary to insert the injection syringe needle all the way through the opening in order to insert the lens-forming material. In the latter case also, the cut 29 simplifies injection.

Figure 3:
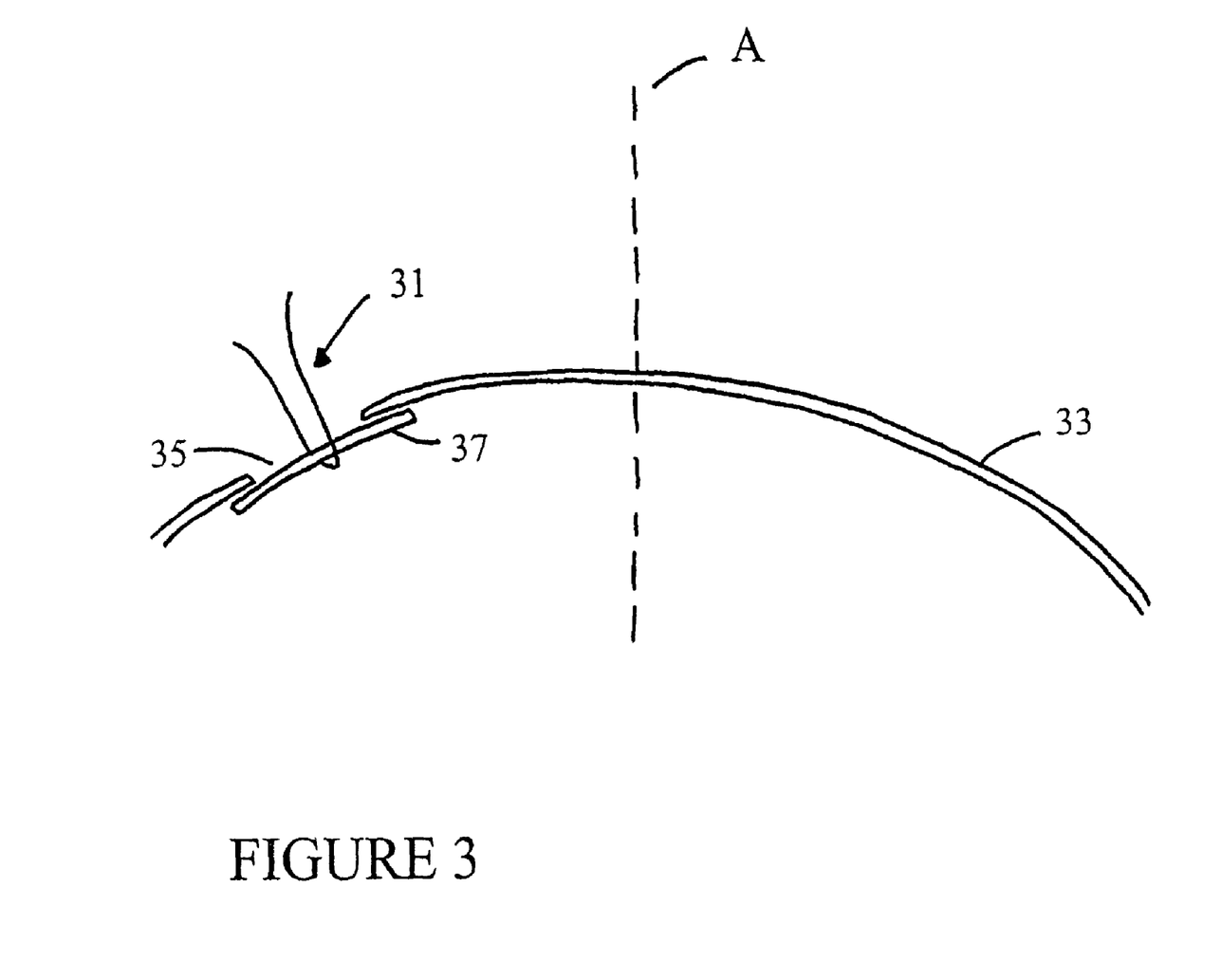
FIG. 3 is a side view of a sealing device prepared using a kit according to an embodiment of the invention, which has been inserted into a capsular bag.

FIG. 3 is a side view of a sealing device 31 of any of the above mentioned kind, which has been inserted into a capsular bag 33 through an opening 35. In this case, the opening 35 is located off the optical axis A of the eye. The opening 35 has a diameter of about 1 mm, and the patch 37 of the sealing device 31 thus has a diameter slightly larger than 1 mm.

Of course the different features described in connection with all embodiments in this section and in the preceding general description may be combined in all possible ways by the skilled person without undue experimentation.

The invention claimed is:

1. Kit comprising a) a disc-shaped collagen patch having a diameter of 0.5-3 mm and a thickness of 5-250 μm, wherein the collagen patch is sufficiently thin to follow the accommodation movements of a capsular bag when the collagen patch is adhered thereto by the adhesive composition, and b) an adhesive composition comprising (i) fibrin, fibrinogen or a combination thereof, and (ii) a biocompatible polymer capable of forming a viscous aqueous solution.

2. Kit according to claim 1, wherein said collagen patch is provided with a removable adjusting means connected to the collagen patch and capable of positioning said collagen patch to a desired location.

3. Kit according to claim 2, wherein the removable adjusting means is at least one flexible thread attached to the collagen patch.

4. Kit according to claim 3, wherein the at least one thread protrudes from the collagen patch.

5. Kit according to claim 1, wherein the collagen patch is adapted to function as a septum to admit passage of an injection device through the patch.

6. Kit according to claim 1, wherein the collagen patch has a cut adapted to admit passage of an injection device through the cut.

7. Kit according to claim 6, wherein the cut is provided with an overlapping part adapted to seal the cut when injection is completed.

8. Kit comprising a) a disc-shaped collagen patch having a diameter of 0.5-3 mm and a thickness of 5-250 μm, and b) an adhesive composition comprising (i) fibrin, fibrinogen or a combination thereof, and (ii) a biocompatible polymer capable of forming a viscous aqueous solution.

9. Kit according to claim 1, wherein said adhesive composition further comprises factor XIII and thrombin.

10. Kit according to claim 1, wherein the adhesive composition comprises said biocompatible polymer in an amount such that an aqueous solution formed from said composition has a viscosity of from 500 to 1,000,000 cP.

11. Kit according to claim 1, wherein the biocompatible polymer capable of forming a viscous solution is a polysaccharide or proteoglycan which does not interfere with the fibrin clotting process.

12. Kit according to claim 11, wherein the biocompatible polymer is selected from the group consisting of xanthan, dextran, cellulose and glycosaminoglycans, and salts and derivatives thereof.

13. Kit according to claim 12, wherein the biocompatible polymer is hyaluronic acid or a salt or derivative thereof.

14. Kit according to claim 1, adapted for use in ophthalmic surgery.

15. A kit according to claim 14, adapted for use in ophthalmic surgery for preparation of a sealing device, wherein the collagen patch of the kit is adapted to seal an opening in a capsular bag of an eye while admitting the entrance of an injection device through the opening for injection of a lens-forming material into the capsule; and wherein the adhesive composition of the kit is adapted to be applied to the collagen patch so as to enable adhesion of the collagen patch to the capsular bag.

16. Kit according to claim 15, wherein the collagen patch is adapted to cover the entire opening.

17. Kit according to claim 15, wherein the collagen patch is adapted to be placed inside of the capsular bag.

18. Kit according to claim 15, wherein the collagen patch is adapted to be placed on the outside of the capsular bag.

19. Kit according to claim 15, wherein the collagen patch is adapted to cover an opening of about 1 mm in diameter.

20. Kit according to claim 15, wherein the opening is situated off an optical axis of the eye.

21. Kit according to claim 15, wherein the collagen patch is sufficiently thin to follow accommodation movements of the capsular bag.

22. Kit according to claim 15, wherein said collagen patch is provided with a removable adjusting means comprising at least one flexible thread, said at least one thread being of a sufficient length to protrude outside of the eye and be manipulated from outside the eye when the collagen patch is positioned to seal the opening.

23. Kit according to claim 15, wherein said sealing device is biodegradable, such that it is degraded within three weeks of being placed in or on a lens capsule.

24. Kit according to claim 23, wherein said sealing device is biodegradable, such that it is degraded within one week of being placed in or on a lens capsule.

25. Kit according to claim 15, wherein said sealing device is biodegradable, such that it is degraded after completion of lens formation.

26. Kit comprising a) a disc-shaped collagen patch, wherein the collagen patch is biodegradable and is operable to degrade within three weeks when employed as a sealing device on or in a lens capsule, and further wherein the collagen patch has a thickness of 5-250 μm and b) an adhesive composition comprising (i) fibrin, fibrinogen or a combination thereof, and (ii) a biocompatible polymer capable of forming a viscous aqueous solution.

27. Kit according to claim 26, wherein the collagen patch is operable to degrade within one week when employed as a sealing device on or in a lens capsule.

28. Kit according to claim 26, wherein the collagen disc has a diameter of 0.5-3 mm.

* * * * *